US010105688B2

(12) United States Patent
Minoux et al.

(10) Patent No.: US 10,105,688 B2
(45) Date of Patent: Oct. 23, 2018

(54) PROCESS FOR PREPARING A MESOPORES-CONTAINING CATALYST, CATALYST THUS OBTAINED AND USE THEREOF IN A HYDROCONVERSION PROCESS

(71) Applicant: TOTAL RAFFINAGE FRANCE, Courbevoiu (FR)

(72) Inventors: Delphine Minoux, Nivelles (BE); Nadiya Danilina, Uccle (BE)

(73) Assignee: TOTAL RAFFINAGE FRANCE, Courbevoie (FR)

( * ) Notice: Subject to any disclaimer, the term of this patent is extended or adjusted under 35 U.S.C. 154(b) by 105 days.

(21) Appl. No.: 14/352,573

(22) PCT Filed: Oct. 24, 2012

(86) PCT No.: PCT/EP2012/071045
§ 371 (c)(1),
(2) Date: Apr. 17, 2014

(87) PCT Pub. No.: WO2013/060719
PCT Pub. Date: May 2, 2013

(65) Prior Publication Data
US 2014/0357909 A1  Dec. 4, 2014

(30) Foreign Application Priority Data

Oct. 24, 2011 (FR) ...................................... 11 59617
Dec. 29, 2011 (FR) ...................................... 11 62519

(51) Int. Cl.
*B01J 29/08* (2006.01)
*B01J 37/06* (2006.01)
(Continued)

(52) U.S. Cl.
CPC .......... *B01J 29/084* (2013.01); *B01J 29/126* (2013.01); *B01J 35/002* (2013.01);
(Continued)

(58) Field of Classification Search
None
See application file for complete search history.

(56) References Cited

U.S. PATENT DOCUMENTS 3,293,192 A   12/1966  Maher et al.
3,506,400 A    4/1970  Eberly, Jr. et al.
(Continued)

FOREIGN PATENT DOCUMENTS

EP    0 082 211 A1    6/1983
EP    0 519 573 B1    4/1992
(Continued)

OTHER PUBLICATIONS

Acid/Base (Neutralization) Reactions, 2010.*
(Continued)

*Primary Examiner* — Melvin C. Mayes
*Assistant Examiner* — Stefanie J Cohen
(74) *Attorney, Agent, or Firm* — Sughrue Mion, PLLC

(57) ABSTRACT

The invention relates to a process for preparing a hydroconverzation catalyst consisting of a modified zeolite Y, comprising the steps of a treatment of a modified zeolite Y by suspension thereof in a basic pH solution, stopping the previous treatment by neutralization of the modified zeolite Y containing solution with an acid-containing solution; filtering and washing the recovered modified zeolite Y solid, drying and optionally calcining the modified zeolite Y solid, placing the modified zeolite Y solid of step d) in contact, with stirring, in an ion exchange solution and optional
(Continued)

steaming and/or calcining the modified zeolite Y type compound for obtaining the catalyst containing a modified zeolite Y.

15 Claims, 2 Drawing Sheets

(51) Int. Cl.
  *B01J 29/12* (2006.01)
  *C10G 47/16* (2006.01)
  *B01J 35/00* (2006.01)
  *B01J 35/10* (2006.01)
  *C07C 1/22* (2006.01)

(52) U.S. Cl.
  CPC .......... *B01J 35/1085* (2013.01); *B01J 37/06* (2013.01); *C07C 1/22* (2013.01); *C10G 47/16* (2013.01); *B01J 2229/14* (2013.01); *B01J 2229/16* (2013.01); *B01J 2229/186* (2013.01); *B01J 2229/22* (2013.01); *B01J 2229/24* (2013.01); *B01J 2229/36* (2013.01); *B01J 2229/37* (2013.01); *B01J 2229/38* (2013.01); *C07C 2529/06* (2013.01)

(56) References Cited

U.S. PATENT DOCUMENTS

| | | | |
|---|---|---|---|
| 4,093,560 | A | 6/1978 | Kerr et al. |
| 5,069,890 | A | 12/1991 | Dai et al. |
| 5,601,798 | A | 2/1997 | Cooper et al. |
| 9,126,183 | B2 * | 9/2015 | Van Donk ............. B01J 29/084 |
| 2012/0018349 | A1 | 1/2012 | Van Donk et al. |

FOREIGN PATENT DOCUMENTS

| | | |
|---|---|---|
| EP | 0 528 494 A1 | 2/1993 |
| WO | 95/07236 A1 | 3/1995 |
| WO | 2010/072976 A1 | 7/2010 |
| WO | WO 2010072976 A1 * | 7/2010 ............ B01J 29/084 |

OTHER PUBLICATIONS

Ogura, et al., "Formation of Uniform Mesopores in ZSM-5 Zeolite through Treatment in Alkaline Solution," *Chem. Letts.*, pp. 882-883 (2000).

Ogura, et al., "Alkali-treatment technique—new method for modification of structural and acid-catalytic properties of ZSM-5 zeolites," *Appl. Catalysis A: General*, v. 219, pp. 33-43 (2001).

Groen, et al., "Optimal Aluminum-Assisted Mesoporosity Development in MFI Zeolites by Desilication," *J. Phys. Chem. B*, v. 108, pp. 13062-13065 (2004).

Groen, et al., "On the introduction of intracrystalline mesoporosity in zeolites upon desilication in alkaline medium," *Mesoporous and Mesoporous Materials*, v. 69, pp. 29-34 (2004).

Van Donk, et al., "Generation, Characterization, and Impact of Mesopores in Zeolite Catalysts," *Catalysis Reviews*, v. 45(2), pp. 297-319 (2003).

Janssen, et al., "Three-Dimensional Transmission Electron Microscope Observations of Mesopores in Dealuminated Zeolite Y," *Angew. Chem. Int. Ed.*, v. 40(6), pp. 1102-1104 (2001).

Krijn P. De Jong, et al., "Zeolite Y Crystals with Trimodal Porosity as Ideal Hydrocracking Catalysts", Angewandte Chemie (International ed. in English), Dec. 27, 2010, 15 pages, vol. 22, No. 52.

W. Lutz, et al., "Determination of the framework and non-framework [$SiO_2$] and [$AlO_2$] species of steamed and leached faujasite type zeolites: calibration of IR, NMR, and XRD data by chemical methods", Microporous and Mesoporous Materials, Sep. 16, 2002, pp. 193-202, vol. 55, No. 2.

V. Calsavara, et al., "On the acidity and/or basicity of USY zeolites after basic and acid treatment", Brazilian Journal of Chemical Engineering, Mar. 2000, 8 pages, vol. 17, No. 1.

Valmir Calsavara, et al., "Reactivity of USY extraframework alumina in alkaline medium", Zeolites, Oct. 1, 1996, pp. 340-345, vol. 17, No. 4.

International Search Report for PCT/EP2012/071045 dated Sep. 11, 2013.

* cited by examiner

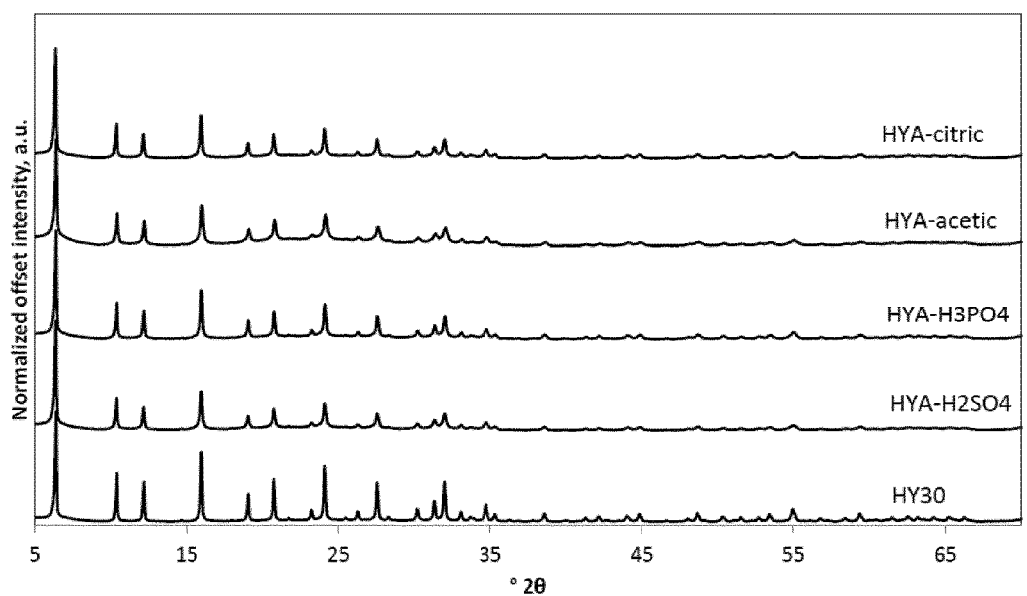
Figure 1. X-ray diffractograms of the parent zeolite CBV760 (HY30), of the modified zeolite neutralized with $H_2SO_4$ (HYA-H2SO4), the modified zeolite neutralized with $H_3PO_4$ (HYA-H3PO4), the modified zeolite neutralized with acetic acid (HYA-acetic), the modified zeolite neutralized with citric acid (HYA-citric)

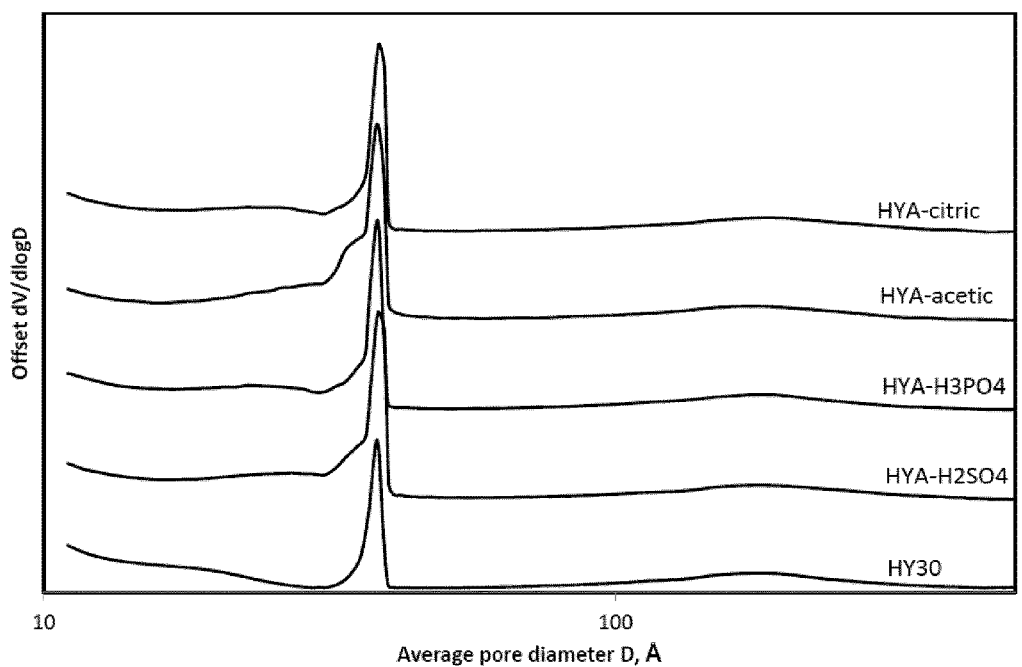
Figure 2. Pore size distribution for the parent zeolite CBV760 (HY30), of the modified zeolite neutralized with $H_2SO_4$ (HYA-H2SO4), the modified zeolite neutralized with $H_3PO_4$ (HYA-H3PO4), the modified zeolite neutralized with acetic acid (HYA-acetic), the modified zeolite neutralized with citric acid (HYA-citric).

PROCESS FOR PREPARING A MESOPORES-CONTAINING CATALYST, CATALYST THUS OBTAINED AND USE THEREOF IN A HYDROCONVERSION PROCESS

CROSS REFERENCE TO RELATED APPLICATIONS

This application is a National Stage of International Application No. PCT/EP2012/071045, filed on Oct. 24, 2012, which claims priority from French Patent Application Nos. 11 59617, filed on Oct. 24, 2011, and 11 62519, filed on Dec. 29, 2011, the contents of all of which are incorporated herein by reference in their entirety.

The invention relates to a process for preparing a mesopores-containing catalyst, the catalyst thus obtained and the use of the catalyst thus obtained in a hydroconversion process.

The catalyst described here comprises a modified zeolite Y and may be used in many hydroconversion processes, in particular, in the hydrocracking process.

The various zeolites are distinguished by different structures and properties, and are well known in the art. A few structures commonly used in the field of catalysis are disclosed in WO2010/072976, among them some are given below.

Zeolite Y (FAU) is a three-dimensional zeolite with large pores, whose structure has large cavities interconnected by channels formed from 12-membered rings, each ring presenting 12 ($Si^{4+}$ and $Al^{3+}$) cations and 12 $O^{2-}$ anions.

Beta zeolite (BEA) is a three-dimensional zeolite with large pores comprising pores formed from 12-membered rings in all directions.

Zeolite ZMS-5 (MFI) is a virtually three-dimensional zeolite with medium-sized pores, comprising pores formed from 10-membered rings in one direction that are interconnected by zig-zag channels formed from 10-membered rings (this is why this structure is considered as being virtually three-dimensional).

Mordenite (MOR) is a zeolite with large pores formed from 12-membered rings, with channels extending in only one direction and which has between these channels small pockets formed from 8-membered rings.

Ferrierite (FER) is a two-dimensional zeolite with medium-sized pores comprising main channels formed from 10-membered rings, which are interconnected via side channels formed from 8-membered rings.

Zeolites are important catalytic materials that are widely used in acidic catalytic reactions such as cracking, especially hydrocracking, FCC and olefin cracking, isomerization reactions, especially of paraffins and olefins, and also in methanol conversion known techniques, for example MTO, MTP and MTG.

For all these reactions, the zeolite is the heart of the catalyst, rendering high catalytic activity, high stability, and last but not least high product selectivity, induced by the microporous zeolite structure. Notwithstanding the positive effect of the presence of micropores with respect to shape selectivity, the micropores may also have a negative impact, which is often illustrated by the low rate of access of molecules into the zeolite crystals, or unwanted adsorption effects of reactants and/or products during the catalytic action. These steric constraints decrease the accessibility of the zeolite micropore volume during the catalytic action, and it can be stated that the zeolite crystals are not always being used effectively.

One of the important issues in the development of new zeolite catalysts is the guarantee of sufficient accessibility of the active sites for reactant and/or product molecules, thereby maximizing the effectiveness of the catalyst. The straightforward solution to minimize diffusion limitation would be the reduction of the intracrystalline diffusion pathlength. One possibility is to decrease the zeolite crystal size. Another strategy to obtain materials with sufficient accessibility is the creation of a secondary pore system consisting of mesopores (2-50 nm) inside the microporous zeolite crystals. Traditionally, mesopores are introduced into zeolites and zeolite-like crystals by dealumination, using hydrothermal treatment such as steaming [U.S. Pat. No. 3,293,192, U.S. Pat. No. 3,506,400, and U.S. Pat. No. 5,069,890], and acid leaching techniques [U.S. Pat. No. 3,506,400, U.S. Pat. No. 4,093,560, and U.S. Pat. No. 5,601,798]. Alternatively, chemical treatments with for example EDTA [U.S. Pat. No. 3,506,400 and U.S. Pat. No. 4,093,560] or $(NH_4)_2SiF_6$ [EP0082211] have been proposed as well. A more detailed literature review on the generation of mesopores in zeolites by various methods, was presented by van Donk et al. [S. van Donk et al., Catalysis Reviews 45 (2003) 297].

Despite of the considerable developments over the last years in the domains of the synthesis, characterization, and comprehension of the formation mechanisms of these structured mesoporous materials, their effective application in industry is still highly limited because of their high cost, which is partially related to the high cost of the organic template. Therefore, from a cost perspective, the classical hydrothermal and acid leaching techniques remain highly attractive, which explains why they are largely used today in industry. However, the introduction of mesopores by these ways is not easily controlled and often materials are obtained with a random and non-optimized mesoporosity. In a paper by Janssen et al. [A. H. Janssen et al., Angew. Chem. Int. Ed. 40 (2001) 1102], it was demonstrated using three-dimensional electron microscopy that a large part of the mesopores in a commercially available steamed and acid leached zeolite Y (CBV 780, Zeolyst Int.) were cavities, not optimally connected to the outer surface of the zeolite crystal. Obviously, for catalysis, a system of interconnected cylindrical mesopores is expected to enhance the accessibility for reactants and the diffusion of reaction products much more than mesoporous cavities inside the crystal.

In recent years, as an alternative to the classical hydrothermal and acid leaching of the as-synthesized zeolite material, another approach for the formation of mesopores has been proposed [M. Ogura et al., Chem. Lett. (2000) 82; M. Ogura, Appl. Catal. A Gen. 219 (2001) 33; J. C. Groen et al., Microporous Mesoporous Mater. 69 (2004) 29; J. C. Groen, et al., J. Phys. Chem. B, 108 (2004) 13062]. This alternative method is based on the careful desilication of the as-synthesized zeolite by a treatment in an alkaline medium. This technique was firstly explored in the late 1980's for studying dissolution phenomena and structural changes in zeolite Y and ZSM-5. Furthermore, two patent applications were assigned to Shell on the modification of ultra-stable and very ultra-stable Y-zeolites with a Si/Al ratio between 2 and 12.5 at/at [EP0528494] and their application in a hydrogenation process [EP0519573].

Recently, the Applicant has disclosed in patent application WO 2010/072 976 a zeolite Y of modified faujasite structure whose intracrystalline structure has trimodal intracrystalline porosity, i.e. three networks of different medium-diameter pores inside each crystal. This zeolite is obtained by using a novel alkaline treatment process on a modified zeolite Y, especially after a dealumination process. This document presents catalytic tests performed on modified zeolite Y powders of trimodal structure onto which a catalytic metal has been deposited. These tests show improved catalytic activity.

However, during the alkaline treatment, an excessive desilication may occur. This excessive basic treatment may lead to the destruction of the material, therefore, causing a loss of crystalline structure of the zeolite and its microporosity. As a result a reduction in the intrinsic activity of the material can be induced.

Thus, the invention is directed towards solving at least one of the problems mentioned above.

DESCRIPTION OF THE INVENTION

According to a first aspect, the invention concerns a process for preparing a hydroconversion catalyst containing a modified zeolite Y, comprising the steps of:
a) treatment of a zeolite Y by suspension thereof in a basic pH solution,
b) stopping the treatment of step a) by neutralization of the zeolite Y containing solution with an acid-containing solution;
c) filtering and washing the recovered modified zeolite Y solid,
d) drying and optionally calcining the modified zeolite Y solid,
e) placing the modified zeolite Y solid of step d) in contact, with stirring, in an ion exchange solution,
f) optional steaming and/or calcining of the modified zeolite Y type compound of step e) for obtaining the catalyst containing a modified zeolite Y.

By applying the neutralization step b), the excessive desilication and the loss of the crystalline structure and the microporosity of the catalyst are avoided.

According to this process, it is rendered possible to obtain a catalyst containing a modified zeolite type compound exhibiting excellent catalytic activity especially regarding hydroconversion reactions of various compounds, such as hydrocarbon feedstock, which is chosen from the group of light cycle oil, atmospheric distillates, vacuum distillates, such as vacuum gasoil, feeds from aromatic extraction units, from solvent dewaxing of base lubricating oils, distillates derived from processes of desulphurisation, deasphalted oils, vegetable or animal oils, oils issued from algae or from bacteria, alone or in mixture.

The step a) includes a treatment of a zeolite Y by suspension thereof in a basic pH solution. The zeolite Y may also be a composite material comprising it, especially at a content of at least 5% by weight relative to the total weight of the composite material.

The solution is preferably an aqueous solution comprising at least one strong base, especially NaOH or KOH, and/or a weak base, in particular, sodium carbonate, sodium citrate, etc., for example, at a concentration ranging from 0.001 to 2 M, at room temperature, under magnetic or mechanical stirring.

The zeolite Y used during step a) of the process preferably presents a bulk Si/Al ratio of greater than or equal to 12.

Such a zeolite Y may be obtained, for example, by applying to a parent zeolite Y at least one dealumination treatment, in particular, a partial dealumination treatment, for example, with at least one acid and/or water vapour. These treatments may lead to (i) reduction in the acidity of the material, (ii) increase, albeit slightly, in the mesoporosity of the initial material, which is theoretically purely microporous. Most particularly, these treatments correspond to those described in U.S. Pat. No. 5,601,798.

In step a), the basic pH solution/zeolite Y weight ratio may range from 20 to 100, especially from 30 to 80, in particular from 40 to 60, or may even be about 50.

The base concentration of the solution of step a) may range from 0.001 to 2 M, especially from 0.005 to 1, in particular from 0.01 to 0.5, or may even be about 0.05 M.

In step a), the placing in contact with a basic solution may last from 5 to 120 minutes, especially, from 10 to 60 minutes and in particular, from 15 to 30 minutes. During this placing in contact, the suspension may be stirred, especially, by magnetic or mechanical stirring.

The neutralization according to step b) may be performed by contacting with any type of acid-containing solution. The acid may be an inorganic or an organic acis, for example, sulphuric, phosphoric, citric, acetic, maleic, pyruvic, levulinic, 2-ketogulonic, keto-gluconic, thioglycolic, 4-acetylbutyric, 1,3-acetonedicarboxylic, 3-oxo propanoic, 4-oxo butanoic, 2,3-diformyl succinic, 5-oxo pentanoic, 4-oxo pentanoic, glycolic, oxamic, glyoxylic acid, EDTA (ethylenediaminetetraacetic acid), nitrilotriacetic acid, N-methylaminodiacetic acid, iminodiacetic acid, diglycolic acid, malic acid, gluconic acid, acetylacetone, tartaric acid, aconitic acid, suberic acid, tricarballylic acid, malonic acid, succinic acid and glycolic acid, formic acid, propionic acid, butyric acid, valeric acid, caproic acid, enantic acid, caprylic acid, pelargonic acid, capric acid, undecylic acid, lauric acid, tridecylic acid, benzoic acid, salicylic acid, glutaric acid, adipic acid, pimelic acid, azelaic acid, phtalic acid, isophtalic acid, lactic acid or a mixture of those, in particular, under industrial conditions, on a large amount of material. The neutralization step may likewise be performed in presence of water. This neutralization is advantageously carried out at room temperature under magnetic or mechanical stirring.

The acid-containing solution is comprising at least one acid, for example, at a concentration ranging from 0.005 to 2 M.

The purpose of the neutralization is to stop the desilication process and to prevent the undesired destruction of the material that can result in extensive loss of crystalline structure of the zeolite, loss of microporosity and induce a decrease in the intrinsic activity of the material.

The process also includes, after the step b), a step c) of filtering the neutralized solution containing the modified zeolite Y by any known means to obtain a solid modified zeolite Y and washing it with a solvent, especially a polar solvent, for example, water.

The modified zeolite Y is then dried (step d)). The drying step may be performed at a temperature greater than or equal to 70° C., especially, greater than or equal to 75° C., or even greater than or equal to 80° C. It may range from one to 36 hours, especially, from one to 24 hours and in particular, from one to 15 hours. The drying may be performed in air or under an inert atmosphere.

The calcination step (step d)) may be performed at a temperature of greater than or equal to 400° C., especially, greater than or equal to 450° C., or even greater than or equal to 500° C. The heating may last from one to 8 hours, in particular, from one to 6 hours, or even from one to 5 hours. The heating may comprise a temperature rise of 0.5 to 2° C./minute and especially, 1° C./minute. The heating may be performed in air or under an inert atmosphere.

In step e), the washed and optionally dried and/or calcined modified zeolite Y, is in contact with a solution, especially an ion exchange aqueous solution, advantageously comprising NH$_4$NO$_3$, especially at a concentration ranging from 0.01 to 0.5 M. This step can be performed several times, for example 2 to 3 times.

The purpose of the ion exchange is to exchange the counter ions of the zeolite framework by a different kind of counter ions and by this introduce a new function into the catalyst. Here, the function is the acidity, therefore, an introduction of protons is required. It is the state-of-art procedure to introduce protons by using ammonium ions first and then subsequently removing ammonia at an elevated temperature. Thus, all compounds dissociating into ammonium ions and not essentially changing the pH of the solution can be used for the ion exchange here. Especially, inorganic ammonium salts are suitable, such as NH$_4$Cl, NH$_4$NO$_3$, (NH$_4$)$_2$SO$_4$ etc.

In step e), the solution containing ammonium ions/zeolite weight ratio may range from 3 to 75, especially, from 3 to 50, in particular, from 4 to 30.

The ammonium salt concentration of the solution, for example the NH$_4$NO$_3$ concentration of the solution, of step e) may range from 0.01 to 0.5, especially, from 0.05 to 0.4, in particular, from 0.1 to 0.3, or may even be about 0.2 M.

Advantageously, step e) can be carried out at room temperature, therefore, does not require heating.

Step e) of placing in contact with the solution containing ammonium ions may last from 1 to 24 hours, especially, from 1 to 12 hours, in particular, from 1 to 8 hours, or even about 1-5 hours. This step may be performed one to three times.

The calcination step f) may be performed at a temperature of greater than or equal to 400° C., especially, greater than or equal to 450° C., or even greater than or equal to 500° C. The heating may last from 1 to 8 hours, in particular, from 1 to 6 hours, or even from 1 to 5 hours.

The heating may comprise a temperature rise of 0.5 to 2° C./minute and especially 1° C./minute.

The heating may be performed in air or under an inert atmosphere.

Optionally, after, instead or before the calcination, a step of treatment with water vapour at a temperature from 250 to 450° C. for 2 to 6 hours is performed. This so-called steaming may help to repair/hydrolyse the bonds with aluminium that may have been broken during the alkaline treatment.

Then, the catalyst essentially consisting of a modified zeolite Y is recovered.

As a result of steps a)-f), a modified zeolite Y catalyst is obtained exhibiting a trimodal intracrystalline porosity, represented by at least one network of micropores, at least one network of small mesopores with a mean diameter of 2 to 5 nm and at least one network of large mesopores with a mean diameter of 10 to 50 nm, these various networks being interconnected.

The modified zeolite Y of the present invention thus has trimodal intracrystalline porosity, i.e. three networks of pores of different mean diameters within each crystal.

More specifically, a trimodal modified zeolite Y may be obtained with a micropore volume that is 20%, especially, 25%, in particular, 30% less than the micropore volume of the starting zeolite Y.

The modified zeolite Y may have a mesopore volume that is 20%, especially 25% higher than the mesopore volume of the starting zeolite Y. In particular, the increase in mesopore volume is essentially due to the creation of small mesopores.

The crystallinity of the modified zeolite with trimodal porosity may be from 40% to 100%.

The modified zeolite Y may have an Si/Al atomic ratio of less than or equal to 25, especially, less than or equal to 24, or even less than or equal to 23, more particularly, less than or equal to 22, even more particularly, less than or equal to 21 and optionally, less than or equal to 20.5.

The Si/Al ratio may also be less than or equal to 40, especially, less than or equal to 35, or even less than or equal to 30, more particularly, less than or equal to 28 and even more particularly, less than or equal to 25.

The Si/Al atomic ratio may be greater than or equal to 6, especially, greater than or equal to 8, or even greater than or equal to 10, more particularly, greater than or equal to 11 and even more particularly, greater than or equal 12.

The Si/Al ratio may also be greater than or equal to 15, especially, greater than or equal to 17, or even greater than or equal to 18, more particularly, greater than or equal to 19 and even more particularly, greater than or equal 20.

The modified zeolite prepared has a total mesopore volume of greater than or equal to 0.20 ml/g, especially greater than or equal to 0.25 ml/g, in particular, greater than or equal to 0.35 ml/g, or even greater than or equal to 0.40 ml/g.

The modified zeolite prepared has a micropore volume of less than or equal to 0.30 ml/g, especially, less than or equal to 0.28 ml/g, in particular, less than or equal to 0.25 ml/g.

The modified zeolite Y prepared may have an external surface area $S_{ext}$ of greater than or equal to 200 m$^2$/g, especially, greater than or equal to 250 m$^2$/g, in particular, greater than or equal to 300 m$^2$/g, or even greater than or equal to 350 m$^2$/g and more particularly, greater than or equal to 400 m$^2$/g.

The acid site density, measured by TPD of ammonia (TPD NH$_3$), may be less than or equal to 0.5 mmol/g, especially less than or equal to 0.48 mmol/g, in particular, less than or equal to 0.46 mmol/g.

The modified zeolite Y generally has the characteristic reflections of a faujasite structure on an X-ray diffraction pattern. These reflections correspond to the following interplane distances: d=13.965, 8.552, 7.293, 5.549, 4.655, 4.276, 3.824, 3.689, 3.232, 2.851, 2.793 and 2.578 Å (reference: Collection of simulated XRD powder patterns for zeolites, fifth revised edition, by M. M. J. Treacy and J. B. Higgins, Elsevier).

The obtained zeolite may be extruded and impregnated with metals, performed according to known methods, chosen from compounds of a metal from group VIII and/or from group VIB, followed by calcination.

During the extrusion, the binder(s) used during may be chosen from the group consisting of alumina, silica, titania, silica-alumina, magnesia and mixtures of one or more of these compounds.

The step of the metal introduction may be an introduction by impregnation or ion exchange of an at least one catalytic metal chosen from the metals of group VIII and/or of group VIB. Group VIB corresponds to group 6 of IUPAC periodic table of the elements (version of Jun. 22, 2007) and comprises Cr, Mo and W. Group VIII (VIIIB) corresponds to groups 8, 9 and 10 of IUPAC periodic table of the elements (version of Jun. 22, 2007) and comprises Fe, Ru, Os, Co, Rh, Ir, Ni, Pd, Pt. Doping agents such as B, P, Si, Zr and Ti can be also added.

Another aspect of the invention concerns a process for the hydroconversion of hydrocarbon feedstock, for example, hydrocracking or hydroisomerization, in which the feedstock to be treated is placed in contact with a catalyst according to the invention, for example, prepared according to the process of the invention.

As a feedstock, light cycle oil, atmospheric distillates, vacuum distillates, such as vacuum gasoil, feeds from aromatic extraction units, from solvent dewaxing of base lubricating oils, distillates derived from processes of desulphurisation, deasphalted oils, vegetable or animal oils, oils issued from algae or from bacteria, alone or in mixture can be used.

Particularly, another aspect of the invention concerns use of the catalyst obtained according to this invention in a hydrocracking process.

Characterization Methods

The methods used to perform the measurements of the various characteristics are generally the standard techniques. More particularly, the following techniques were used in the context of this invention:

i) the chemical composition, in particular, the bulk Si/Al atomic ratio and the Pt content, was determined by X-ray fluorescence spectroscopy;

ii) the structure of the zeolite was defined by X-ray diffraction (XRD). XRD was conducted on a Bruker D8 Discover diffractometer in the range between 5 to 70° with a Cu $K_{\alpha 1}$ radiation using a step-size of 0.02° and time/step of 1 s. The relative crystallinity of the samples was determined by background subtraction method;

iii) the nitrogen adsorption and desorption measurements were performed at the temperature of liquid nitrogen on a Micromeritics Tristar 3000 machine. Before each measurement, the samples were degassed under nitrogen at 300° C. for 840 minutes. The textural properties, defined by the external surface area ($S_{ext}$), the micropore volume ($V_{micro}$) and the mesopore volume ($V_{meso}$), were identified by volumetry with nitrogen using adsorption isotherms recorded at 77 K by applying the state-of-the-art methods [Barett, E. P.; Joyner, L. G.; Halenda, P. P. *J. Am. Chem. Soc.* 1951, 73, 373-380. Rouquerol, F.; Rouquerol, J.; Sing, K. *Adsorption by powders and porous solids*; Academic Press: San Diego, 1999]. The BET method [S. Brunauer, P. H. Emmett and E. Teller, *J. Am. Chem. Soc.,* 1938, 60, 309] was used to calculate the specific surface area. The external specific surface area and the specific pore volume were determined by the t-plot method, an empirical semi-quantitative method based on the comparison of the isotherm adsorption data of a porous sample and a non-porous sample of identical chemical composition and surface nature [K. S. W. Sing, Chem. and Ind., (1968) 1520]; the statistical thickness was calculated by means of the Harkins-Jura formula. The t-plot method is based on the comparison of the isotherm adsorption data for a porous sample and for a non-porous sample of identical chemical composition and surface nature;

iv) the acidity of the catalysts was established by programmed thermo-desorption of ammonia (TPD $NH_3$) between 100 and 650° C. [Niwa, M.; Iwamoto, M.; Segawa, K. B. *Chem. Soc. Jpn.* 1986, 59] by monitoring the desorbed ammonia by conductivity;

v) the shape and the size of the crystals as well as the porosity within particular crystals were characterized by transmission electron microscopy and scanning electron microscopy.

The invention is now described with reference to the attached non-limiting drawings, in which:

FIG. 1 represents the X-ray diffractograms of the parent zeolite Y (CBV760—Zeolyst Int.), of the modified zeolite Y neutralized with $H_2SO_4$ (HYA-H2SO4), neutralized with $H_3PO_4$ (HYA-H3PO4), neutralized with acetic acid (HYA-acetic) and neutralized with citric acid (HYA-citric).

FIG. 2 shows the pore size distribution for the parent zeolite Y (CBV760—Zeolyst Int.), of the modified zeolite Y neutralized with $H_2SO_4$ (HYA-H2SO4), neutralized with $H_3PO_4$ (HYA-H3PO4), neutralized with acetic acid (HYA-acetic) and neutralized with citric acid (HYA-citric).

EXAMPLES

The parent zeolite Y (CBV760, Zeolyst Int.) is referred to as HY30. The characteristics of HY30 are given in Table 1 and graphically represented in FIGS. 1 and 2.

Example 1: Preparation of a Modified Zeolite Y Catalyst Neutralized with $H_2SO_4$ (HYA-H2SO4)

The compound HY30 is subjected to the following alkaline treatment:

HY30 (20 g) is placed in contact with an aqueous 0.05 M NaOH solution (250 ml) for 15 minutes at room temperature and under stirring, after 15 minutes, a solution of 1M $H_2SO_4$ is added to the suspension during 5-10 minutes to reach a pH of 7, the resulting product is filtered off and washed with water, the filtered product is dried overnight at 80° C., aqueous 0.20 M $NH_4NO_3$ solution (250 ml) is added to the dry product, and the whole is left for 5 hours at room temperature under stirring. This manipulation is performed trice, the product obtained is washed with water, the product is then calcined at 500° C. for 4 hours (temperature gradient of 1° C./minute) in a stream of air, and then the HYA-H2SO4 is recovered.

The characteristics of the samples are given in Table 1, graphically represented in FIGS. 1 and 2 and discussed in Example 5.

Example 2: Preparation of Modified Zeolite Y Catalyst Neutralized with $H_3PO_4$ (HYA-H3PO4)

The compound HY30 is subjected to the following alkaline treatment:

HY30 (20 g) is placed in contact with an aqueous 0.05 M NaOH solution (250 ml) for 15 minutes at room temperature and under stirring, after 15 minutes, a solution of 1M $H_3PO_4$ is added to the suspension during 5-10 minutes to reach a pH of 7, the resulting product is filtered off and washed with water, the filtered product is dried overnight at 80° C., aqueous 0.20 M $NH_4NO_3$ solution (250 ml) is added to the dry product, and the whole is left for 5 hours at room temperature under stirring. This manipulation is performed trice, the product obtained is washed with water, the product is then calcined at 500° C. for 4 hours (temperature gradient of 1° C./minute) in a stream of air, and then the HYA-H3PO4 is recovered.

The characteristics of the samples are given in Table 1, graphically represented in FIGS. 1 and 2 and discussed in Example 5.

Example 3: Preparation of a Modified Zeolite Y Catalyst Neutralized with Acetic Acid (HYA-Acetic)

The compound HY30 is subjected to the following alkaline treatment:
  HY30 (20 g) is placed in contact with an aqueous 0.05 M NaOH solution (250 ml) for 15 minutes at room temperature and under stirring,
  after 15 minutes, a solution of 1M acetic acid is added to the suspension during 5-10 minutes to reach a pH of 7,
  the resulting product is filtered off and washed with water,
  the filtered product is dried overnight at 80° C.,
  aqueous 0.20 M $NH_4NO_3$ solution (250 ml) is added to the dry product, and the whole is left for 5 hours at room temperature under stirring. This manipulation is performed trice,
  the product obtained is washed with water,
  the product is then calcined at 500° C. for 4 hours (temperature gradient of 1° C./minute) in a stream of air, and then
  the HYA-acetic is recovered.

The characteristics of the samples are given in Table 1, graphically represented in FIGS. 1 and 2 and discussed in Example 5.

Example 4: Preparation of a Modified Zeolite Y Catalyst Neutralized with Citric Acid (HYA-Citric)

The compound HY30 is subjected to the following alkaline treatment:
  HY30 (20 g) is placed in contact with an aqueous 0.05 M NaOH solution (250 ml) for 15 minutes at room temperature and under stirring,
  after 15 minutes, a solution of 1M citric acid is added to the suspension during 5-10 minutes to reach a pH of 7
  the resulting product is filtered off and washed with water,
  the filtered product is dried overnight at 80° C.,
  aqueous 0.20 M $NH_4NO_3$ solution (250 ml) is added to the dry product, and the whole is left for 5 hours at room temperature under stirring. This manipulation is performed trice.
  the product obtained is washed with water,
  the product is then calcined at 500° C. for 4 hours (temperature gradient of 1° C./minute) in a stream of air, and then
  the HYA-citric is recovered.

The characteristics of the samples are given in Table 1, graphically represented in FIGS. 1 and 2 and discussed in Example 5.

Example 5: Characterization of the Compounds HY30, HYA-H2SO4, HYA-H3PO4, HYA-Acetic and HYA-Citric X-Ray Diffraction FIG. 1 shows the X-ray diffractograms of the parent zeolite Y (CBV760) (HY30), of the modified zeolite Y catalyst neutralized with $H_2SO_4$ (HYA-H2SO4), neutralized with $H_3PO_4$ (HYA-H3PO4), neutralized with acetic acid (HYA-acetic) and neutralized with citric acid (HYA-citric). All diffractograms are corresponding to zeolite Y (faujasite structure). The crystallinity of the samples is decreasing in the order: HY30>HYA-citric≥HYA-H3PO4≤HYA-H2SO4>HYA-acetic (Table 1).

Nitrogen Sorption

Table 1 gives the BET surface area, the external surface area, the total, the microporous and the mesoporous pore volumes of the parent zeolite Y (CBV760) (HY30), of the modified zeolite Y catalyst neutralized with $H_2SO_4$ (HYA-H2SO4), neutralized with $H_3PO_4$ (HYA-H3PO4), neutralized with acetic acid (HYA-acetic) and neutralized with citric acid (HYA-citric). The surface area is smaller for the NaOH-treated samples, whereas it is higher for HYA-citric and HYA-H3PO4 than for HYA-H2SO4 and HYA-acetic. The external surface area is correspondingly higher for the mesoporized samples. The microporous volume decreases after the NaOH-treatment. HYA-H3PO4 and HYA-citric possess the highest microporous volumes among HYA samples. The mesoporous volume is increasing due to the NaOH-treatment.

FIG. 2 shows the pores size distribution of all samples. HY30 shows only one broad peak at around 19 nm. The peaks at around 4 nm are an analytical anomaly. The NaOH-treated and neutralized HYA samples have an additional peak at around 2.8 nm, corresponding to small mesopores.

Temperature-Programmed Desorption of Ammonia (TPD-$NH_3$)

Table 1 shows the overall acidity of the parent zeolite Y CBV760 (HY30), of the mesoporized zeolite neutralized with $H_2SO_4$ (HYA-H2SO4), neutralized with $H_3PO_4$ (HYA-H3PO4), neutralized with acetic acid (HYA-acetic) and neutralized with citric acid (HYA-citric) respectively. It is lower for HYA samples. Among HYA samples, HYA-H3PO4 and HYA-citric possess the highest overall acidity. This correlates with the microporous volume.

CONCLUSION

Table 1 summarizes the most important characteristics of all samples. All samples possess a faujasite structure, however, the crystallinity of the HYA samples is lower than that of the parent HY30. During the NaOH-treatment, the surface area is decreasing as well as the microporous volume, whereas the mesoporous volume and especially the volume of small mesopores (2-8 nm) is increasing. The overall acidity correlates with the microporous volume.

Within the HYA samples, HYA-H3PO4 and HYA-citric maintain the highest surface area, microporous volume and overall acidity still showing considerable amount of mesopores. This might be explained by their lower acidity and the polyprotic nature.

TABLE 1

Summary of the characterization results of HY30, HYA-H2SO4, HYA-H3PO4, HYA-acetic and HYA-citric

| Sample | | HY30 | HYA-H2SO4 | HYA-H3PO4 | HYA-acetic | HYA-citric |
|---|---|---|---|---|---|---|
| Crystallinity | % | 95 | 68 | 70 | 55 | 71 |
| Si/Al bulk | | 24.3 | 30.1 | 29.4 | n.d.[a] | n.d.[a] |
| $S_{BET}$[b] | m²/g | 938 | 765 | 797 | 685 | 816 |
| $S_{ext}$[c] | m²/g | 107 | 287 | 236 | 379 | 245 |
| $V_{tot}$[d] | ml/g | 0.549 | 0.533 | 0.533 | 0.426 | 0.546 |
| $V_{micr}$[e] | ml/g | 0.339 | 0.199 | 0.235 | 0.128 | 0.24 |

TABLE 1-continued

Summary of the characterization results of HY30, HYA-H2SO4, HYA-H3PO4, HYA-acetic and HYA-citric

| Sample | | HY30 | HYA-H2SO4 | HYA-H3PO4 | HYA-acetic | HYA-citric |
|---|---|---|---|---|---|---|
| $V_{meso}{}^f$ | ml/g | 0.21 | 0.30 | 0.28 | 0.34 | 0.28 |
| TPD-NH$_3$ | mmol/g | 0.47 | 0.39 | 0.45 | 0.39 | 0.43 |

$^a$ not determined;
$^b$ BET surface area;
$^c$ external surface area;
$^d$ total pore volume;
$^e$ microporous volume;
$^f$ mesoporous volume.

Example 6: Catalysis—Hydrocracking of Squalane

The samples HY30, HYA-H2SO4, HYA-H3PO4, HYA-acetic and HYA-citric containing 0.5 wt % Pt were catalytically tested in hydrocracking of squalane (Alfa Aesar, 98.8%). The tests were performed using plug-flow reactors at following operating conditions:
H$_2$ pressure: 20 barg
Temperature: 180-300° C.
WHSV: 3 h$^{-1}$
H$_2$/squalane ratio: 4 mol/mol.

The tests were performed using 1 mL of catalyst (sieved to 120-160 μm), activated at 450° C. (1° C./min) for 4 h in a flow of hydrogen.

The invention claimed is:

1. A process for preparing a hydroconversion catalyst consisting essentially of a modified zeolite Y, comprising the steps of:
    a) treatment of a zeolite Y by suspension thereof in a basic pH solution,
    b) stopping the treatment of step a) by neutralization of the zeolite Y containing solution with an acid-containing solution consisting essentially of acetic acid,
    c) filtering and washing the recovered modified zeolite Y solid,
    d) drying and optionally calcining the modified zeolite Y solid,
    e) placing the modified zeolite Y solid of step d) in contact, with stirring, in an ion exchange solution,
    f) optionally steaming the modified zeolite Y type compound,
    g) calcining the modified zeolite Y type compound optionally steamed, this modified zeolite being a part of the composition of a final catalyst.

2. The process according to claim 1, wherein the base concentration of the solution of step a) may range from 0.001 to 2 M, preferably from 0.005 to 1, more preferably from 0.01 to 0.5, or may even be about 0.05 M.

3. The process according to claim 1, wherein, in step a), the basic pH solution/zeolite Y weight ratio is in the range of 20 to 100.

4. The process according to claim 1, wherein the concentration of the acid solution is ranging from 0.001 to 2 M.

5. The process according to claim 1, wherein the washing step c) is carried out with a solvent.

6. The process according to claim 1, wherein the calcination step of step d) is performed at a temperature of greater than or equal to 400° C.

7. The process according to claim 1, wherein, in step e), the modified zeolite Y is in contact with an ion exchange aqueous solution including ammonium ions at a concentration ranging from 0.01 to 0.5 M.

8. The process according to claim 1, wherein, after step e), a washing step is performed using a solvent.

9. The process according to claim 1, wherein the base concentration of the solution of step a) may range from 0.005 to 1.

10. The process according to claim 1, wherein the base concentration of the solution of step a) may range from 0.01 to 0.5.

11. The process according to claim 1, wherein, in step a), the basic pH solution/zeolite Y weight ratio is in the range of 30 to 80.

12. The process according to claim 1, wherein, in step a), the basic pH solution/zeolite Y weight ratio is in the range of 40 to 60.

13. The process according to claim 5, wherein the solvent is a polar solvent.

14. The process according to claim 8, wherein the solvent is a polar solvent.

15. The process according to claim 1, wherein the final catalyst also contains at least one metal selected from groups VIII and/or VIB.

* * * * *

UNITED STATES PATENT AND TRADEMARK OFFICE
CERTIFICATE OF CORRECTION

PATENT NO. : 10,105,688 B2  
APPLICATION NO. : 14/352573  
DATED : October 23, 2018  
INVENTOR(S) : Delphine Minoux and Nadiya Danilina Page 1 of 2

It is certified that error appears in the above-identified patent and that said Letters Patent is hereby corrected as shown below:

On the Title Page

<u>Item (57), ABSTRACT</u>

Line 2, delete "consisting of" and insert --comprising-- therefor;

Line 3, delete "modified zeolite Y" and insert --zeolite Y-- therefor;

Line 5, delete "the modified zeolite" and insert --the zeolite-- therefor;

Line 9, delete "of step d)" and insert --obtained from previous step-- therefor;

Page 2, Line 2, delete "the catalyst" and insert --the hydroconversion catalyst-- therefor;

In the Specification

Column 3, Line 19, delete "comprising" and insert --including-- therefor;

Column 3, Line 32, delete "the catalyst" and insert --the hydroconversion catalyst-- therefor;

Column 4, Lines 47-48, delete "a solid modified zeolite Y" and insert --a modified zeolite Y solid-- therefor;

Column 4, Line 50, delete "zeolite Y" and insert --zeolite Y solid-- therefor;

Column 4, Line 65, delete "the washed and optionally dried and/or calcined" and insert --the washed (step c)) and dried and optionally calcined-- therefor;

Column 4, Line 66, delete "zeolite Y" and insert --zeolite Y solid-- therefor;

Signed and Sealed this  
Twenty-ninth Day of October, 2019

Andrei Iancu  
*Director of the United States Patent and Trademark Office*

CERTIFICATE OF CORRECTION (continued)
U.S. Pat. No. 10,105,688 B2

Column 4, Line 67 to Column 5, Line 1, delete "comprising $NH_4NO_3$" and insert --including ammonium ions-- therefor;

Column 5, Line 40, delete "calcination" and insert --calcination (step f))-- therefor;

Column 6, Line 6, delete "Si/Al ratio" and insert --Si/Al atomic ratio-- therefor;

Column 7, Line 66, delete "Int.)" and insert --Int.) (HY30)-- therefor;

Column 8, Line 4, delete "Int.)" and insert --Int.) (HY30)-- therefor.